US011484210B1

(12) United States Patent
Abdul Raheem Ahmed

(10) Patent No.: US 11,484,210 B1
(45) Date of Patent: Nov. 1, 2022

(54) METHODS AND SYSTEMS FOR EARLY DETECTION OF DIABETES AND ADVISING THOSE CONSIDERED PRE DIABETIC OR DIABETIC

(71) Applicant: Waleed Bahaa El Deen Abdul Raheem Ahmed, Asyut (EG)

(72) Inventor: Waleed Bahaa El Deen Abdul Raheem Ahmed, Asyut (EG)

( * ) Notice: Subject to any disclaimer, the term of this patent is extended or adjusted under 35 U.S.C. 154(b) by 202 days.

(21) Appl. No.: 16/446,786

(22) Filed: Jun. 20, 2019

(51) Int. Cl.
*A61B 5/145* (2006.01)
*A61B 5/0205* (2006.01)
*A61B 5/00* (2006.01)
*A61B 5/021* (2006.01)

(52) U.S. Cl.
CPC ........ *A61B 5/0205* (2013.01); *A61B 5/14532* (2013.01); *A61B 5/4833* (2013.01); *A61B 5/7275* (2013.01); *A61B 5/742* (2013.01); *A61B 5/7475* (2013.01); *A61B 5/021* (2013.01)

(58) Field of Classification Search
None
See application file for complete search history.

(56) References Cited

U.S. PATENT DOCUMENTS

| | | | | |
|---|---|---|---|---|
| 6,152,880 A * | 11/2000 | Okada | ............... | A61B 5/02233 600/485 |
| 2004/0197846 A1* | 10/2004 | Hockersmith | ..... | A61B 5/14532 435/14 |
| 2006/0020186 A1* | 1/2006 | Brister | ................ | A61B 5/6848 600/345 |
| 2007/0073173 A1* | 3/2007 | Lam | ...... | A61B 5/6898 600/490 |
| 2008/0091089 A1* | 4/2008 | Guillory | .............. | A61B 5/4094 600/301 |
| 2009/0312620 A1* | 12/2009 | Chang | ..................... | G16Z 99/00 600/365 |
| 2011/0245634 A1* | 10/2011 | Ray | .................... | A61B 5/14532 600/309 |
| 2012/0095309 A1* | 4/2012 | Price | ...................... | G16H 70/20 600/365 |
| 2012/0271557 A1* | 10/2012 | Sekimoto | ............. | A61B 5/4866 702/19 |
| 2014/0058237 A1* | 2/2014 | Galley | ............... | A61B 5/14532 600/365 |
| 2017/0215811 A1* | 8/2017 | Newberry | .............. | G16H 40/63 |
| 2017/0300186 A1* | 10/2017 | Kuhar | .................. | A61B 5/7445 |
| 2017/0329917 A1* | 11/2017 | McRaith | ................ | G16H 10/20 |
| 2018/0110472 A1* | 4/2018 | Lonnroth | ........... | A61B 10/0051 |
| 2018/0116560 A1* | 5/2018 | Quinn | .................. | A61B 5/6832 |
| 2018/0256103 A1* | 9/2018 | Cole | ...................... | G16H 20/60 |
| 2019/0132801 A1* | 5/2019 | Kamath | ................ | G16H 10/65 |
| 2019/0142313 A1* | 5/2019 | Abou Ismail | ...... | A61B 5/14532 600/316 |
| 2019/0159720 A1* | 5/2019 | Geronimo-Button | ...... | A61B 5/1118 |

* cited by examiner

Primary Examiner — Etsub D Berhanu

(57) ABSTRACT

Disclosed herein are methods and systems for a medical device that can monitor at least one chronic condition for example diabetes, with improved features that enable the device to detect the case while it is still pre diabetes, this early detection may significantly postpones the disease and minimizes complications with the change of life style, additionally it can advise those considered diabetics about their treatment protocol if it is sufficient or needs adjustment as the disease progresses.

2 Claims, 10 Drawing Sheets

METHODS AND SYSTEMS FOR EARLY DETECTION OF DIABETES AND ADVISING THOSE CONSIDERED PRE DIABETIC OR DIABETIC

CROSS-REFERENCE TO RELATED APPLICATIONS

Not applicable.

STATEMENT REGARDING FEDERALLY SPONSORED RESEARCH OR DEVELOPMENT

Not applicable.

THE NAME OF THE PARTIES TO AJOINT RESEARCH AGREEMENT

Not applicable.

REFERENCE TO A SEQUENCE LISTING

Not applicable.

BACKGROUND-DISCUSSION OF PRIOR ART

This section provides background information related to the present disclosure which is not necessarily prior art.

Diabetes mellitus is a carbohydrate metabolism disorder caused by insufficient insulin production and or reduced sensitivity to insulin. Consequently the cells are inhibited from normal glucose utilization, resulting in abnormally high blood sugar levels and a variety of maladies. Chronic complications include diabetic retinopathy (retinal changes leading to blindness), kidney disease and frequent infections. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes. Advances in the field of electronics over the past several years have brought about significant changes in medical diagnostic and monitoring equipment, including arrangements for self-care monitoring of various chronic conditions. With respect to the control and monitoring of diabetes, relatively inexpensive and relatively easy-to-use blood glucose monitoring systems have become available that provide reliable information that allows a diabetic and his or her healthcare professional to establish, monitor and adjust a treatment plan (diet, exercise, and medication). More specifically, microprocessor-based blood glucose monitoring systems are being marketed which sense the glucose level of a blood sample that is applied to a reagent-impregnated region of a test strip that is inserted in the glucose monitor. When the monitoring sequence is complete, the blood glucose level is displayed by, for example, a liquid crystal display (LCD) unit. Nowadays there are noninvasive devices which are a needle-free, they can measure glucose concentration without finger pricking, by using infra red waves, ultrasonic waves, laser and many other techniques, also there are continues glucose monitoring technology, in which an electrode with different forms is implemented within the diabetic individual and sends data wirelessly to a computing devices. Some of these monitoring devices from any mentioned techniques are able to upload the results to a server to be revised by healthcare professionals; some may contain an alarm to a predetermined threshold. Although an early detecting of the disease significantly minimizes the complications, none of these devices detect if the user is normal, pre diabetic or diabetic to early deal with the condition and however the accepted glucose fasting and postprandial ranges in diabetic patients are different from normal ranges; for example the accepted fasting blood glucose level for a diabetic patient in some references may be less than 126 mg/dl however this concentration for a person who considers himself as normal is a pre diabetic or a diabetic case and some medical actions or life style changes should be taken to postpone the development of the disease and minimizing complications, while the prior art is directed to control blood glucose in diabetic patients, it fails to early detect pre diabetes or even diabetes in individuals considering themselves as normal. So it is apparent from the above that there is a need for a smart device that advices the user if he is normal, pre diabetic or diabetic.

Advantages

Thus several advantages of one or more aspects are that early detection of a chronic disease for example diabetes, while it is still pre diabetes or at the early beginning of the disease, detecting it while it is pre diabetes can significantly delay the disease progression by applying the right life style, and detecting the disease at the early beginning can minimize the complications. The system also can advise those considered diabetics if their treatment protocol needs adjustment as the disease progresses. These and other advantages of one or more aspects will become apparent from a consideration of the ensuing description and accompanying drawings.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below. One advantage of the present invention is an Early detection of the chronic diseases such as diabetes, which is considered crucial to minimize complications, however modern electronic devices, especially microprocessor based can guide the diabetic patients, there is no device that can early detect and advise the users—especially those with high risk factors such as family history and obesity—about their diabetes state. In one embodiment of the present invention the device is able to detect if the user is normal, pre diabetic or diabetic and guiding the user thereof. In another embodiment the device is able to advice the diabetic patient if he is on the right treatment protocol or the treatment protocol needs to be adjusted.

The above summary of the present invention is not intended to represent each embodiment, or every aspect, of the present invention. Additional features and benefits of the present invention are apparent from the detailed description, and figures set forth below. It is understood that diabetes is an example of any chronic disease and the present disclosure can be practiced with any other chronic diseases without departure from the present invention scope or spirit.

(10) Drawings—Reference Numerals

| | |
|---|---|
| 10 input device | 20 processor |
| 30 memory device | 40 output device |
| 50 condition 1 sensor | 60 condition N sensor |
| 70 glucose monitoring device | 80 touch screen |
| 90 test strip | 100 prompting message |
| 110 soft key | 120 soft key |
| 130 soft key | 140 soft key |
| 150 message | 160 result |
| 170 exemplary message | 180 Glucose monitoring device |
| 190 LCD | 200 Control button(s) |
| 210 flowchart step | 220 flowchart step |
| 230 flowchart step | 240 flowchart step |
| 250 flowchart step | 260 flowchart step |
| 270 device | 280 touch screen |
| 290 prompting message | 300 soft key |
| 310 soft key | 320 biochemical strip |
| 330 cuff | 340 flowchart step |
| 350 flowchart step | 360 flowchart step |
| 370 flowchart step | 380 flowchart step |
| 390 flowchart step | |

DETAILED DESCRIPTION OF THE INVENTION

One or more specific embodiments of the present invention will be described below, reference is made to the accompanying drawings which form a part hereof, and in which is shown by way of illustration different embodiments in which the invention may be practiced. These embodiments are described in sufficient detail to enable those skilled in the art to practice the invention, and it is to be understood that other embodiments may be utilized and that logical, other changes may be used without departing from the spirit or scope of the present invention.

Figure 1:
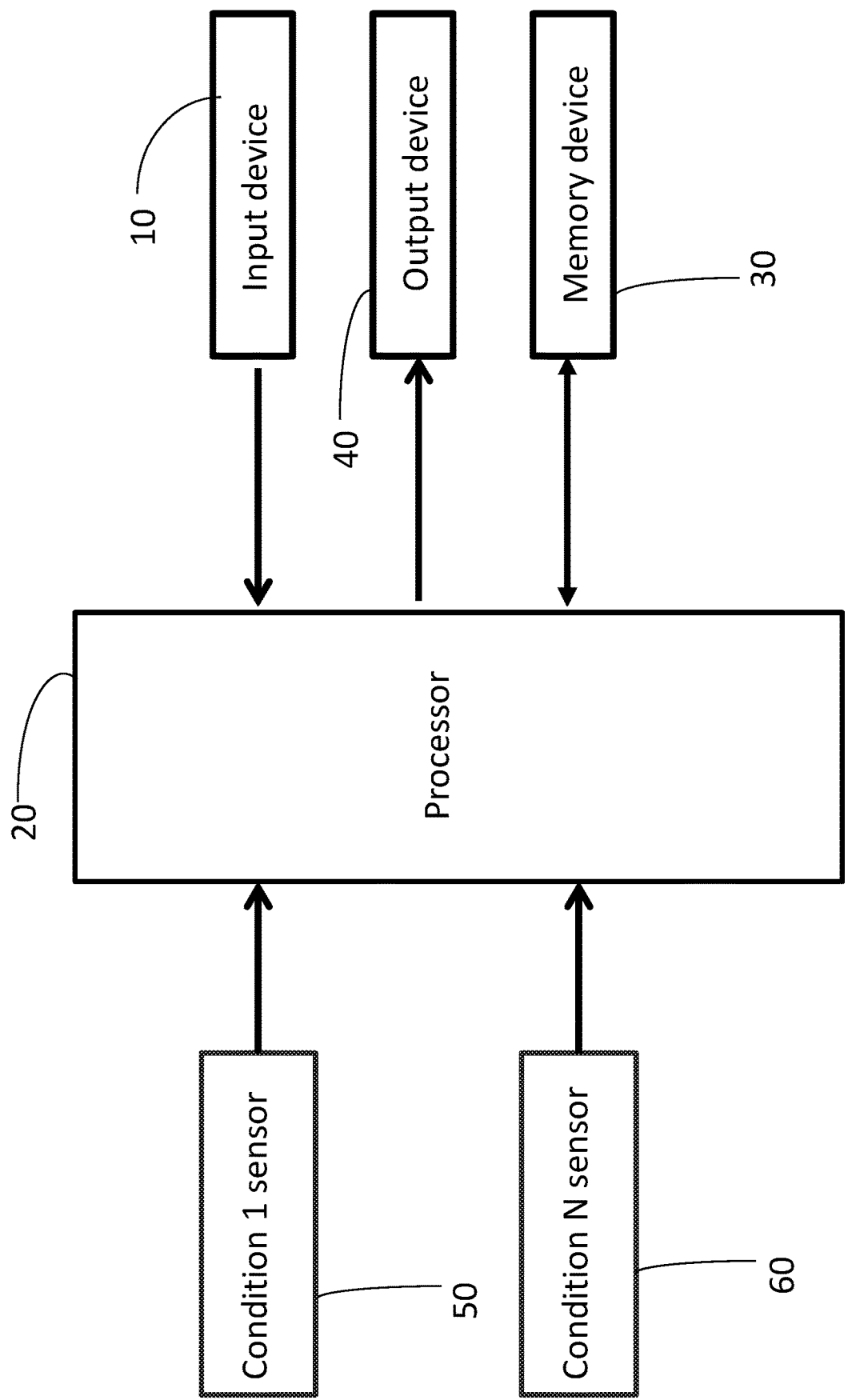
FIG. 1 is a block diagram illustrates the first embodiment.

FIG. 1 is a block diagram illustrates the first embodiment, an output device 40 is connected to at least one processor 20, the output device 40 is one of a group comprising but not limiting (LCD, sensitive touch screens or any other equivalents), an input device 10 is connected to the processor 20, the input device 10 may be a keypad, a touch screen or any other arrangements, FIG. 1 also shows at least one memory device 30 containing at least one program and is connected to the processor 20, the memory device 30 is of any type or it can be any electronic arrangement that can store a program and/or data, it is known to those skilled in the art that the processor 20 with the memory 30 can be replaced with a microcontroller or any other arrangement without departure from the present invention spirit or scope. FIG. 1 also shows a condition 1 sensor 50 connected to the processor 20, the condition 1 sensor 50 in at least one embodiment is an analyte sensor of any type. FIG. 1 also shows a condition N sensor 60 connected to the processor 20. The condition N sensor 60 is any numbers of physiological sensors for example blood pressure sensor as described in the alternative embodiment.

Operation:

The present embodiment is a method and a system that can advise a user about at least one chronic health condition (for example diabetes), based on at least one diagnosing factor (for example blood glucose level), thus early detection of a related disease can be achieved. For example it can be used to early detect diabetes; the accepted blood glucose limits for diabetics are different from the accepted limits for normal individuals; the fasting blood glucose range for the normal individuals in some references is for example from 70 mg/dl to 100 mg/dl while from 100 mg/dl to 125 mg/dl is considered a pre diabetic case according to some references, and above 125 mg is considered a diabetic case while in diabetics the accepted value for fasting individual according to some references is for example less than 126 mg/dl, and the postprandial range for normal individuals according to some references is for example less than 140 mg/dl while the accepted range for diabetics according to some references is for example less than 180 mg/dl.

FIG. 1 shows, the output device 40 prompts the user to select or enter one of his physiological states for example if he is diabetic or non diabetic, the user select or enter his physiological condition with the input device 10, a condition 1 sensor 50, senses a condition which may be an analyte concentration such as blood glucose concentration, a processor 20 executes a program stored in the memory device 30 to: (1) calculate the condition value sensed by the condition 1 sensor 50, (2) compare the measured value with a stored threshold limit in the memory device 30, this stored threshold is related to the user's physiological condition entered or selected by the input device 10, (3) puts a conclusion regarding the presence or absence of the physiological condition at the output device 40, the conclusion may be an alarm, advising message, visual or audio monitory. It is known to those skilled in the art that the condition 1 sensor may be analyte sensor such as blood glucose sensor either biochemical strips, continuous glucose monitoring means or non invasive means.

Figure 2A:
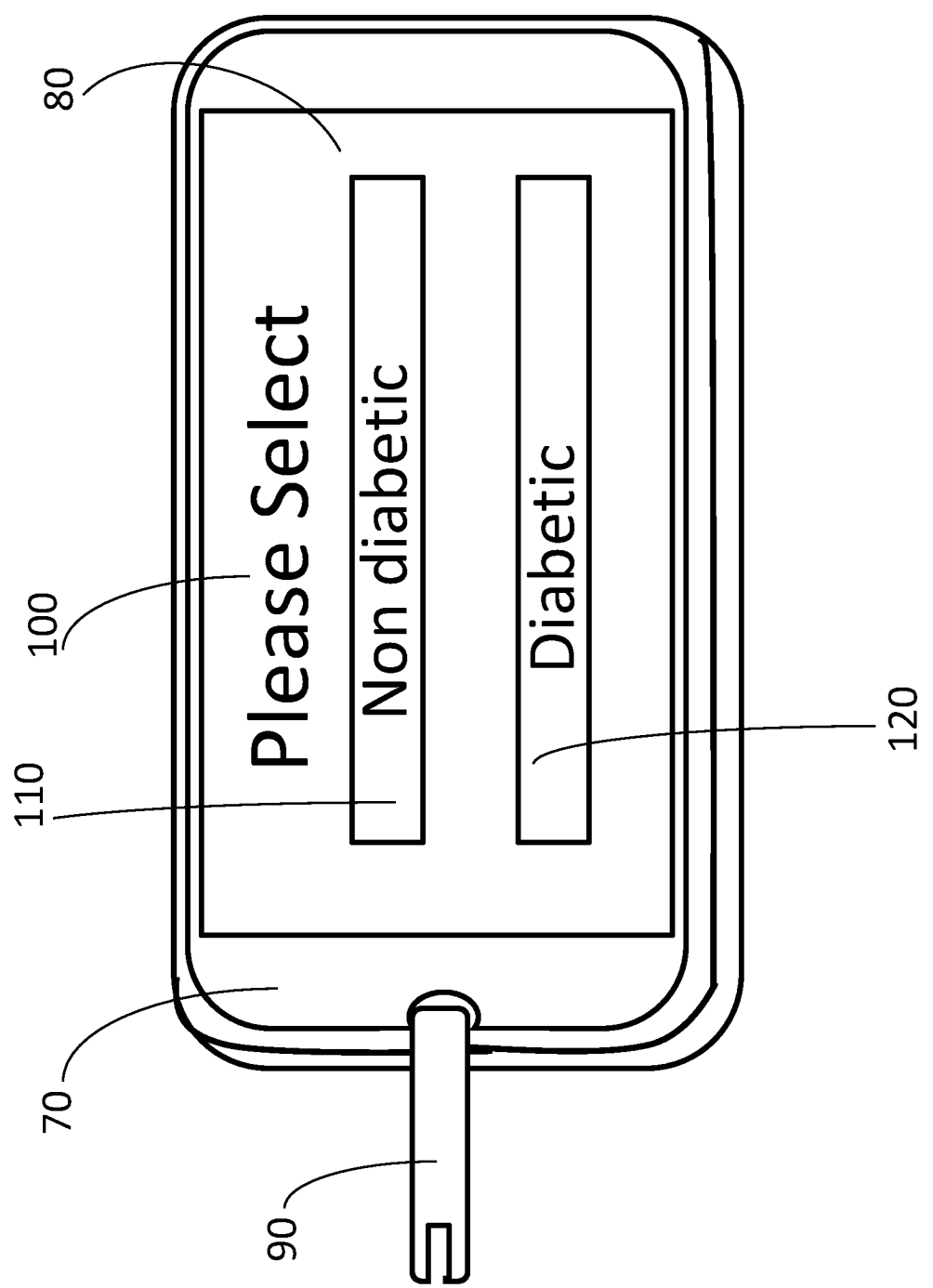
FIG. 2a to FIG. 2f illustrates an example to practice the first embodiment.

FIG. 2a to FIG. 2f illustrate an example to practice the first embodiment to early detect a chronic health condition (diabetes) while it is still in pre case (pre diabetes) using one diagnosing factor (blood glucose level), the example shows, in FIG. 2a, a glucose monitoring device 70, employing a touch screen 80 as an input/output device, a prompting message 100 asking the user to select if he considers himself as a non diabetic (soft key 110) or a diabetic (soft key 120), if the user selects that he is a non diabetic, a second screen appears (FIG. 2b) with a prompting message 100 asking the user to select if he is fasting (soft key 130) or postprandial (soft key 140), if the user selects that, he is fasting, a third screen appears (FIG. 2c) with a message 150 Ready to start the test, the user drop the blood sample at the test strip 90, a forth screen appears with the result message 160 (FIG. 2d), assuming the result is 125 mg/dl however this blood glucose concentration is accepted for a fasting diabetic individual it is not accepted for a one considered normal, so a fifth screen appears which is the advising screen (FIG. 2e) informing the user with an exemplary message 170 about the normal target and suggesting that the user may be in a pre diabetic case and advising the user to see his doctor. The message 170 is varying according to the user category, test type and the result, examples of different messages according to the test type, user category and the result:

(1) if the user category is a non diabetic, the test type is fasting and the result ranges from 70 mg/dl to 100 mg/dl, the message 170 for example will be (You are OK), while if the result ranges from 100 mg/dl to 125 mg/dl the message 170 for example will be (The appropriate rang for your category is between 70 and 100 mg/dl, a pre diabetic case may be exist, Check with your physician).

(2) if the user category is non diabetic, the test type is postprandial and the result is less than 140 mg/dl, the message 170 for example will be (You are OK), while if the result is greater than 140 mg/dl the message 170 for example will be (The appropriate rang for your selections is less than 140 mg/dl, a diabetic case may be exist, Check with your physician). It should be obvious that, the above examples of the advising message 170 are of explanatory purpose and they may be updated according to the updates of diabetes guidelines.

It is obvious to those skilled in the art that, the soft key 110 (designated as non diabetic) and the soft key 120 (designated as diabetic) is a way to change the device mode between regular glucose monitoring mode and pre diabetes check and they can be described as pre diabetes check and blood glucose check or any other description without departure from the present invention spirit or scope.

It is obvious to those skilled in the art that, the soft key 130 (designated as fasting) and the soft key 140 (designated as postprandial) can be changed to low range and high range or any other description without departure from the present invention spirit or scope.

(FIG. 2*f*) describes an alternate to practice the present embodiment;

in which the blood glucose monitor 180 with LCD 190 and control button(s) 200 is used, the user selects his category and the test type by using the control button(s), and the result and the advising message are displayed on the LCD 190 as described above.

It is obvious to those skilled in the art that the control button (s) is used to switch the device between regular glucose monitoring and pre diabetes check. Since using button to change a microprocessor based device mode is a mature technology; so it is not described in details in the above embodiment, it is obvious to those skilled in the art that there are plenty of ways to achieve it for example by making the button put a signal on one of the processor inputs or by long press and make the processor measures the time of pressing if exceeds certain time; the processor changes the device mode or by number of pressing and so on.

Thus the present embodiment overcomes the prior art disadvantages such as: (a) focusing only on diabetics, (b) using fixed thresholds only for the accepted diabetic ranges, (c) and also the present embodiment helps in early detection of the disease while it is still pre diabetes which markedly postpones the disease and minimizes the complications.

It should be known that however all glucose levels mentioned in the above examples and descriptions are referenced with at least one reference, they are all of illustrative purpose to make better understanding of the present disclosure and it is not limiting to this ranges and the intention is to make the idea clear and to better understanding that the normal blood glucose levels are different from the accepted blood glucose levels for diabetics and the present invention overcomes the prior art limitations in early detecting the case while it is still pre diabetes. All glucose ranges mentioned here may be updated according to the diabetes guidelines updates.

It should be obvious to those skilled in the art that, the above examples use a handheld glucose meter with a biochemical test strip to explain the first embodiment, and not to limit the present disclosure to such devices; any other glucose monitoring can utilize the same embodiment, for example continuous glucose monitoring techniques, such as implementing electrode within the individual or using tattoos electrodes and so on, also a noninvasive glucose monitoring techniques including wearable devices can utilize the same embodiment without departure from the present disclosure spirit or scope.

Figure 2B:
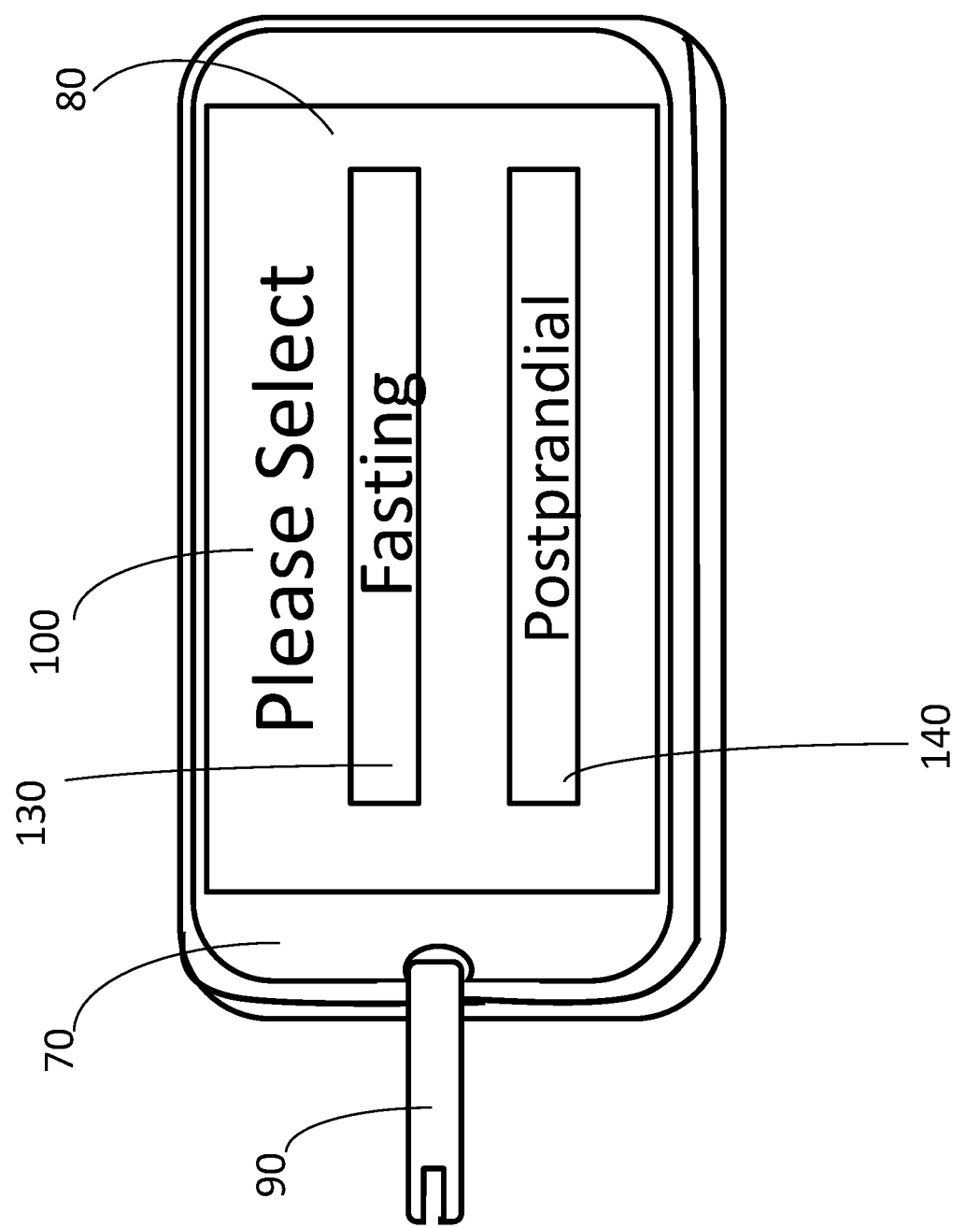
Figure 2C:
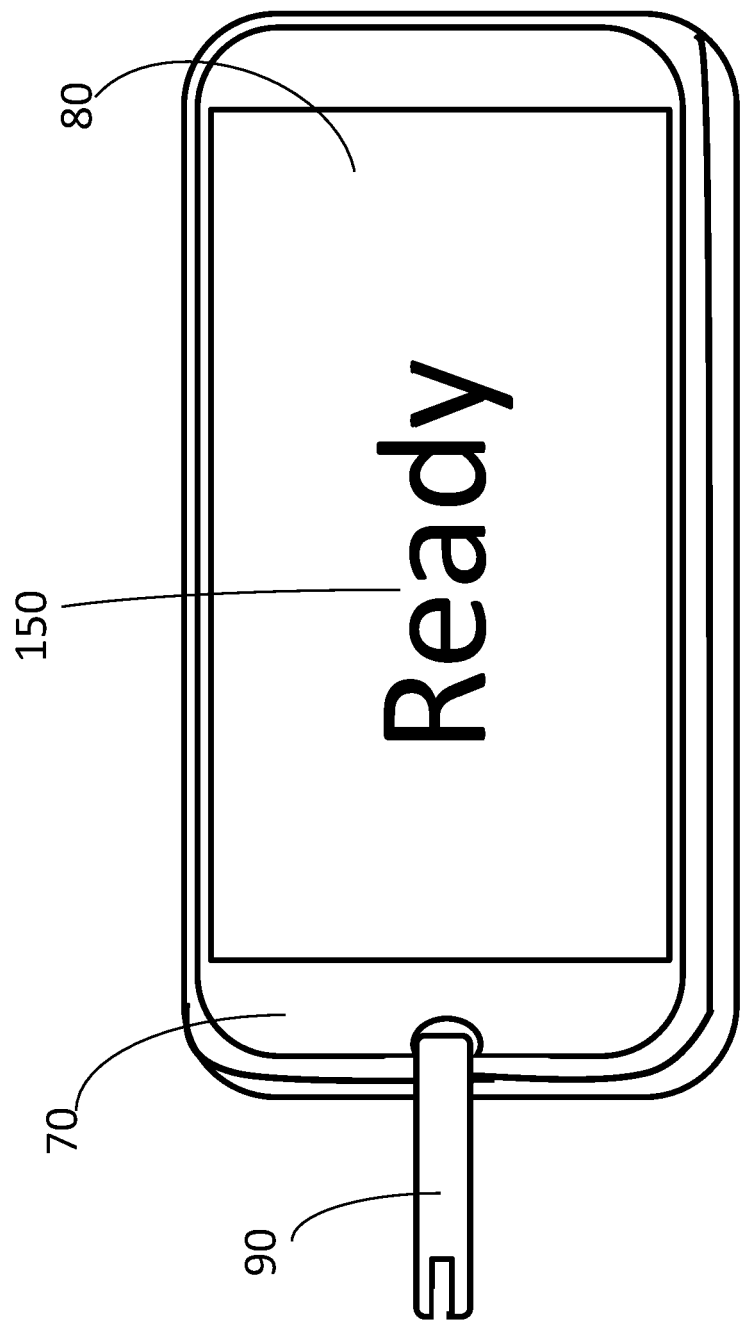
Figure 2D:
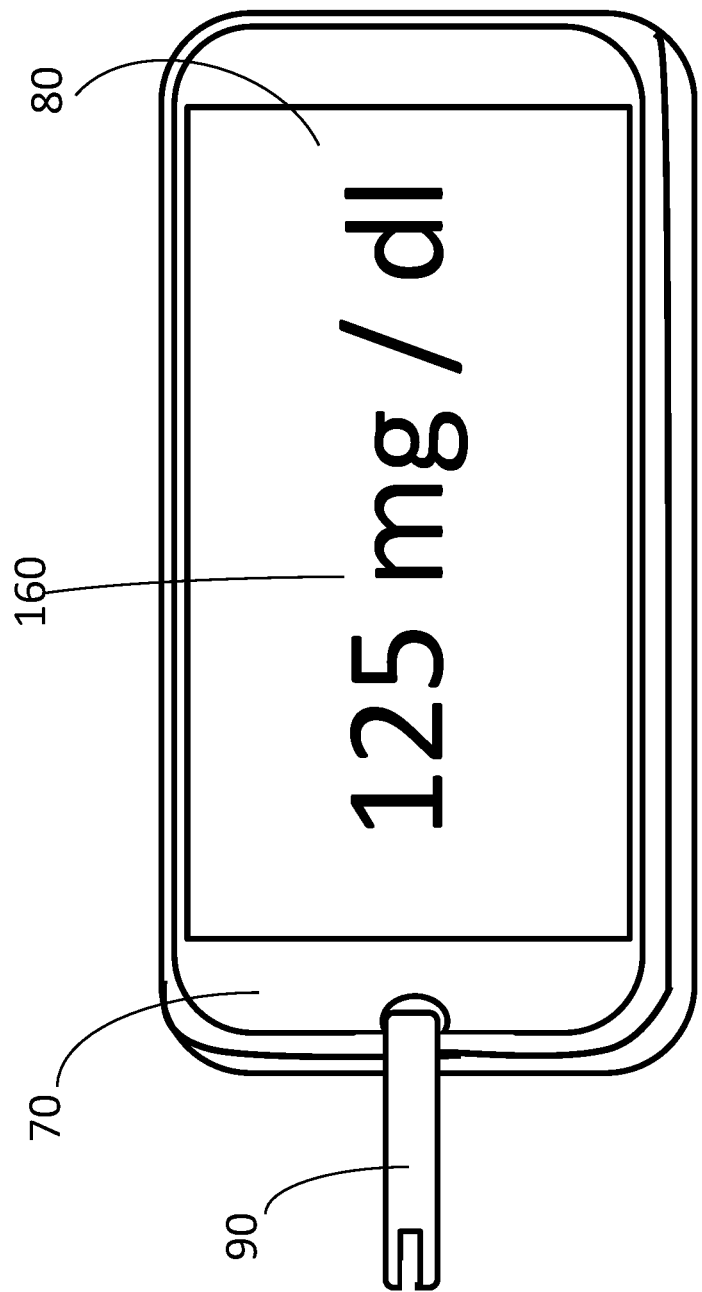
Figure 2E:
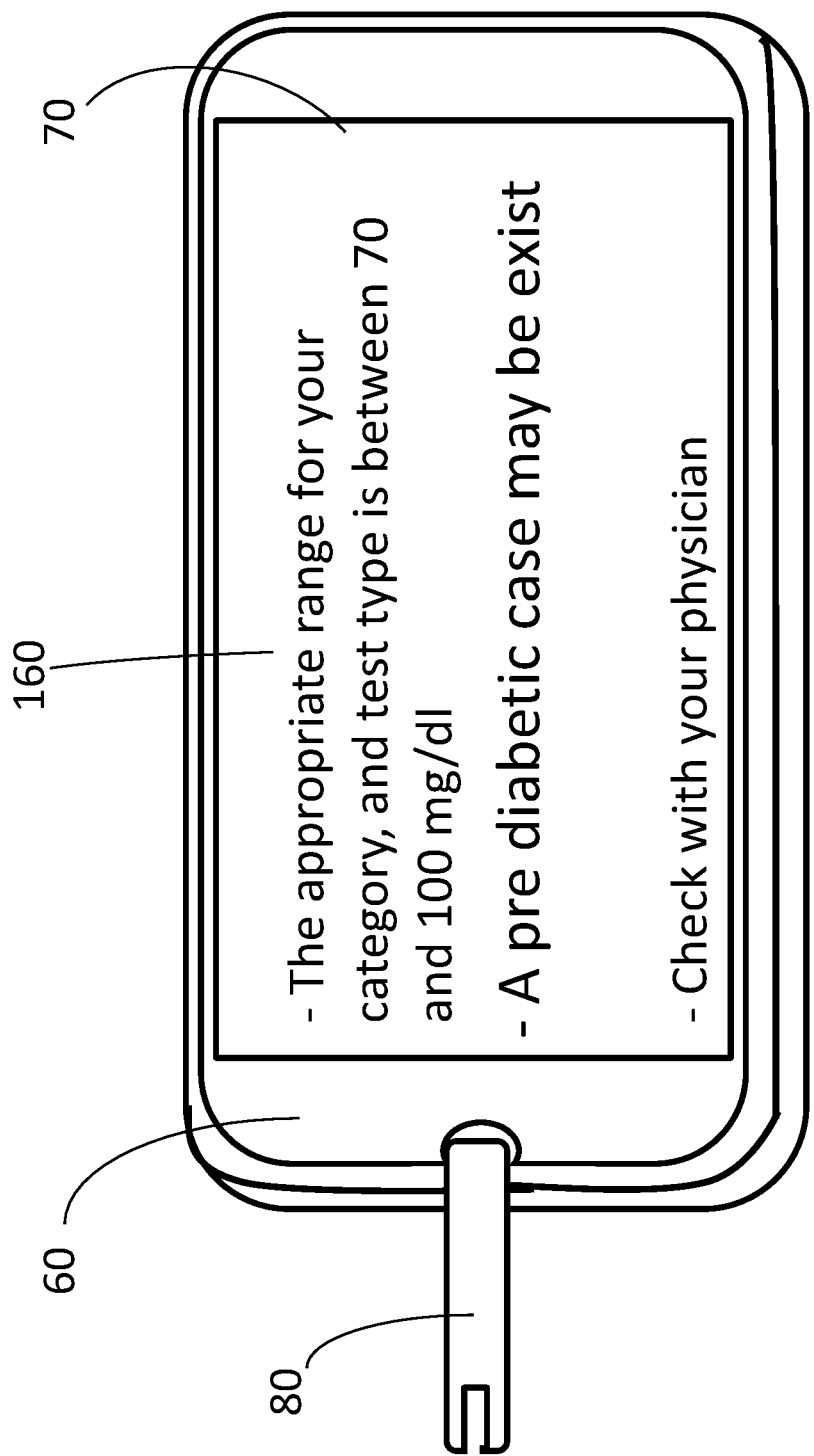
Figure 2F:
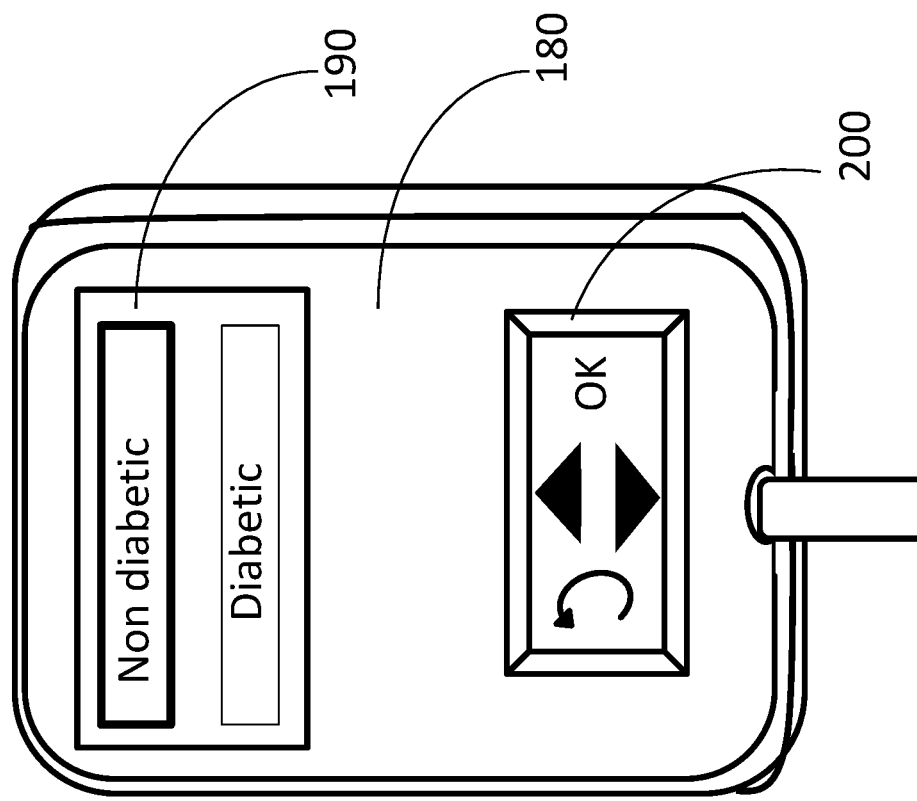

In one embodiment the present invention also advising the diabetic patient about their current treatment protocol if it is sufficient or needs to be adjusted, for example (1) if the user selects diabetic soft key 120 FIG. 2*a* and selects the test type fasting soft key 130 FIG. 2*b* if the result for example is less than 125 mg/dl the advising message 170 FIG. 2*e* will be for example (you are OK), else if the result ranges for example from 120 mg/dl to 160 mg/dl the message 170 FIG. 2*e* for example will be (your target should be less than 125 mg/dl, your medicine and/or your life style may need to be changed, check with your physician). And if the result is for example higher than 160 mg/dl the message 170 FIG. 2*e* may be (call your doctor as soon as possible).

(2) if the user selects diabetic soft key 120 FIG. 2*a* and selects the test type postprandial soft key 140 FIG. 2*b* and if the result for example is less than 180 mg/dl the advising message 170 FIG. 2*e* will be for example (you are OK), else if the result is higher than 180 mg/dl the message 170 FIG. 2*e* for example will be (your target should be less than 180 mg/dl, your medicine and/or life style may need to be changed, check with your physician). And if the result is for example higher than 220 mg/dl the message 170 FIG. 2*e* may be (call your doctor as soon as possible).

Thus according to this embodiment the user is guided, if his treatment is still sufficient or needs to be adjusted as the disease progresses. It should be known that however all glucose levels mentioned in the above examples and descriptions are referenced with at least one reference, they are all of illustrative purpose to make better understanding of the present disclosure and it is not limiting to this ranges, and the intention is to make the idea clear. All mentioned glucose levels are subjected to updates according to the updated diabetes guidelines.

It is obvious to those skilled in the art that, glucose monitoring (glucose meters) devices are mature technology, there are plenty of US patents describing in sufficient details such devices either invasive or noninvasive. Examples of US patents which cover invasive devices: U.S. Pat. No. 9,477,811 B2, dated Oct. 25, 2016, by Steven Drucker, Oakland, Calif. (US), U.S. Pat. No. 6,989,243 B2, dated Jan. 24, 2006, by Adva Yani, Milpitas, Calif. (US) and U.S. Pat. No. 6,881,578 B2, dated Apr. 19, 2005, by Gary Otake, Union City, Calif. (US). And an example of noninvasive glucose monitoring is U.S. Pat. No. 9,167,993 B2, dated Oct. 27, 2015.

Figure 3:
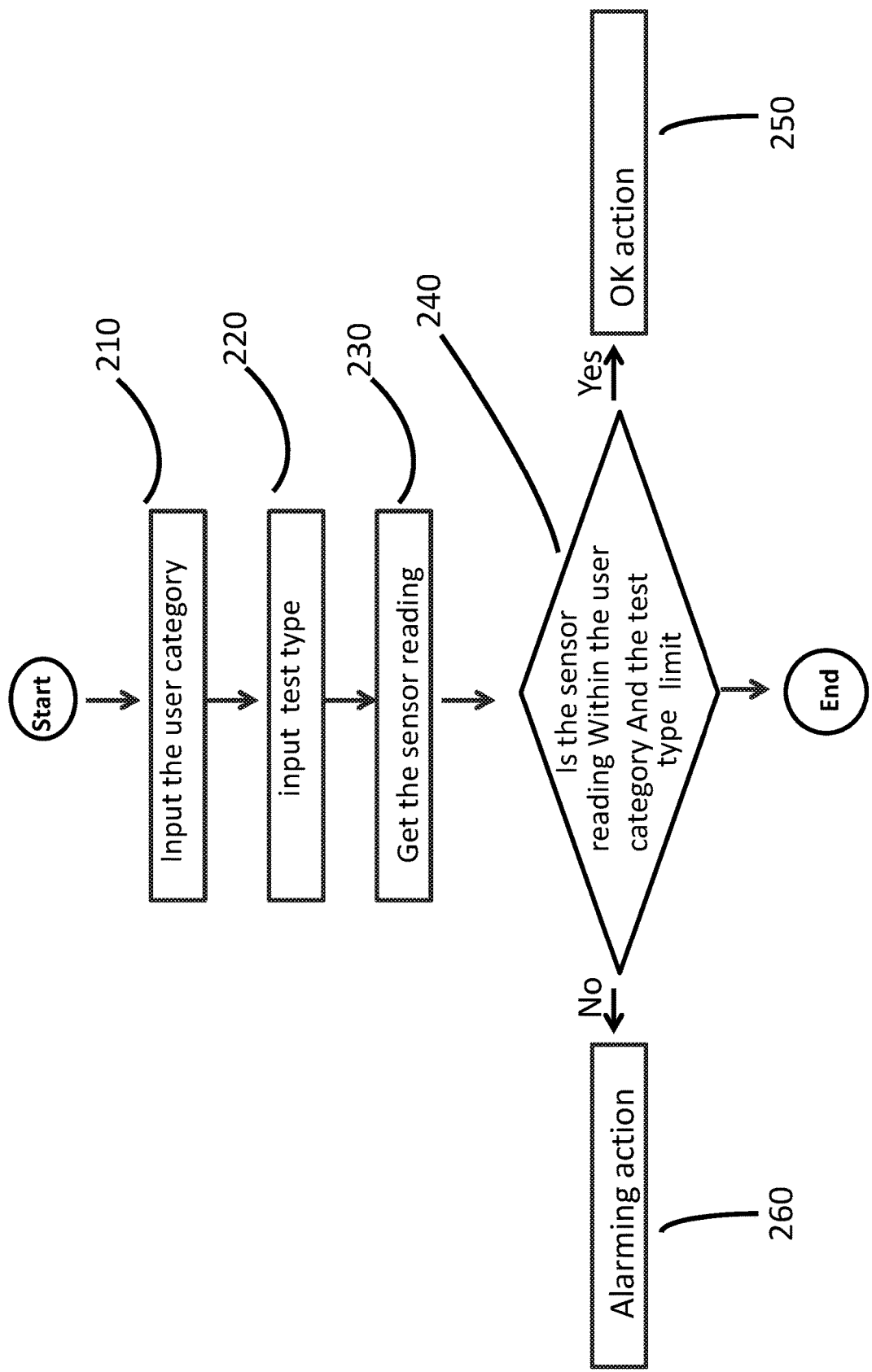
FIG. 3 illustrates a flowchart showing an example to practice the first embodiment.

It should be obvious that using touch screens as an input output devices is a mature technology, the prior art describes in sufficient details how to employ touch screen, one example is U.S. Pat. No. 8,427,817 B2, dated Apr. 23, 2013, by Joseph B. Lewis, Indianapolis, Ind. (US). FIG. 3 illustrates a flowchart showing an example to practice the first embodiment, in the first step 210 the user is prompted to select what is physiological category he believes that he is belonging, in one embodiment the user selects either a non diabetic or diabetic, the second step 220 the user is prompted to select the test type, in one embodiment the user selects either fasting blood glucose test or postprandial blood glucose test, the third step 230 is to get the sensor reading, the forth step 240 is to decide if the sensor reading Within the user Category and the test type threshold, if yes a message 250 appears to inform the user that he is OK, if No an alarming message 260 appears to inform the user about his condition and the suitable action that should be taken.

Figure 4:
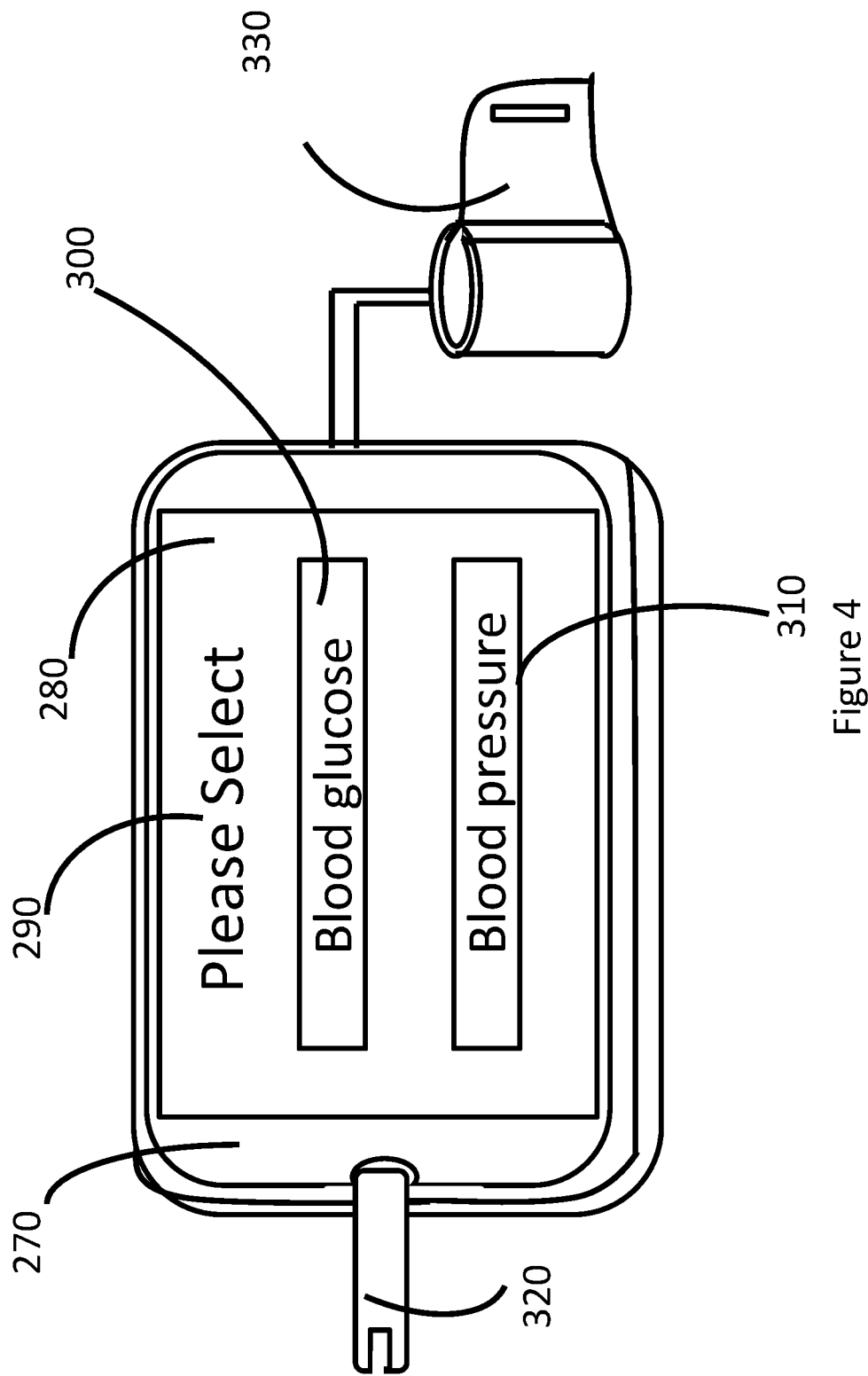
FIG. 4 illustrates an alternative embodiment.

FIG. 4 illustrates an alternative embodiment, the figure shows a device 270, with a touch screen 280 acting as an input/output device, the figure shows a biochemical strip 320 attached to the device 270 and also a cuff 330 attached to the device 270. It is obvious to those skilled in the art that the above description in the first embodiment can be practiced with any other chronic health condition (chronic disease) that in which the accepted limits in patients are different from normal ranges, for example the accepted limits for blood pressure in normal (non diabetic) individuals according to at least one reference are different from the accepted limits in diabetic patients, so the first embodiment can be practiced with hypertension patients as in the alternative embodiment as follows: (1) the user selects his category if he is diabetic or non diabetic as described in the first embodiment FIG. 2a by pressing the conformable soft key either the soft key 110 for the non diabetic or the soft key 120 for diabetic, (2) a second screen appears as screen 280 FIG. 4 with a prompting message 290, asking the user to select the chronic health condition to be measured either blood glucose by pressing the soft key 300 or blood pressure by pressing the soft key 310, (3) the user will select blood pressure, the processor 20 in FIG. 1 will communicate with the condition N sensor 60 FIG. 1 to get the measured blood pressure value, (4) the processor 20 FIG. 1 compares the measured value with the threshold of the specific user category (diabetic or non diabetic) stored in the memory 30 FIG. 1, (5) if the measured value is greater than the threshold the processor 20 puts the corresponding alarming action, which may be audio alarming tone, light or an advising message appears on the screen 280 FIG. 4.

Figure 5:
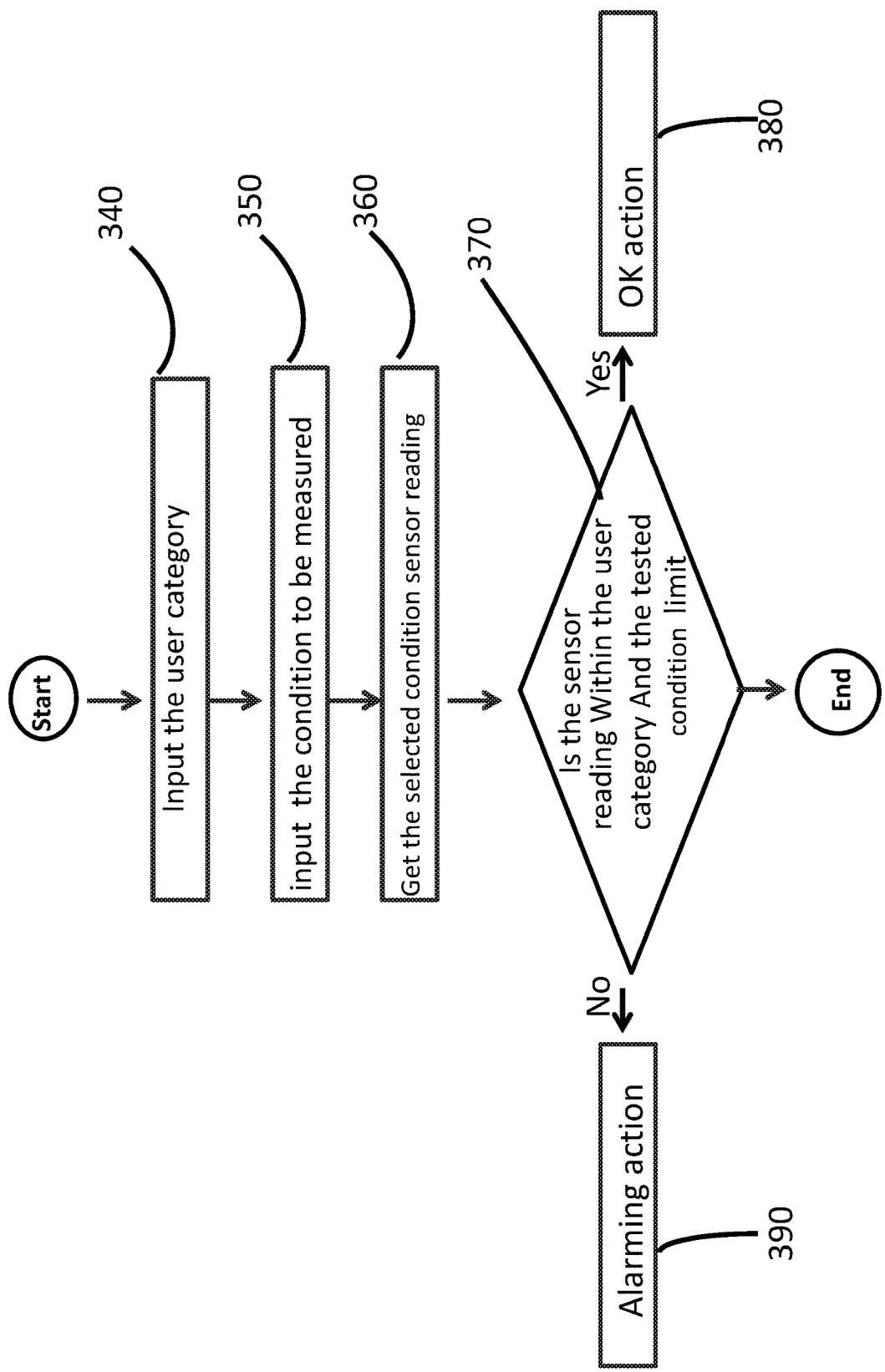
FIG. 5 illustrates a flowchart showing an example to practice the alternative embodiment.

FIG. 5 illustrates a flowchart showing an example to practice the alternative embodiment, in the first step 340 the user is prompted to select what is physiological category he believes that he is belonging, in one embodiment the user selects either a non diabetic or diabetic, the second step 350 the user is prompted to select which condition to be measured, in one embodiment the user selects either blood glucose test or blood pressure test, the third step 360 is to get the selected condition sensor reading, the forth step 370 is to decide if the sensor reading Within the user category and the tested condition limit, if yes a message 380 appears to inform the user that he is OK, if No an alarming message 390 appears to inform the user about his condition and the suitable actions that should be taken.

It should be obvious to those skilled in the art that, measuring blood pressure with microprocessor based devices is a mature technology now and the prior art describes how to achieve it with sufficient details; so it is not described with the alternative embodiment.

While the above description contains many specificities, these should not be construed as limitations on the scope, but rather as an exemplification of one [or several] embodiment(s) thereof. Many other variations are possible. For example In one embodiment, a hypoglycemic limit is stored on the memory device 30 FIG. 1 and if the processor 20 FIG. 1 detects a hypoglycemic level, it will put an alarming action at the output device 40 FIG. 1, the alarming action may be audio alarming tone, or alarming message appears at the sensitive touch screen 80 FIG. 2e or any other suitable action.

In one embodiment, all measurements are stored on the memory device 30 FIG. 1 to be revised by the health care professionals.

In another embodiment, all measurements may be submitted over the internet to health care professionals or may be uploaded to a server to be used for any purpose for example it may be used for counting the newly discovered patients.

In one embodiment the user enters an ID that saves his category and the usually performed test type, to not enter his category or test type each time he uses the device.

It is obvious to those skilled in the art that one or more described embodiments can be practiced by using a mobile phone or any other computing device connected to the condition sensor via Bluetooth, USB, or any other communication method as a standalone application or as a part of any other health mobile applications, without departure from the present invention spirit or scope.

Sequence Listing

Not applicable.

I claim:

1. A device for early detection of prediabetes in real time using a single blood glucose concentration and not insulin as a diagnosing factor, the device comprising:

at least one processor, at least one memory device storing at least one program, a condition sensor connected to said at least one processor and configured to sense a blood glucose level, an input device connected to said at least one processor and configured to allow a user to select either a diabetes check mode or a prediabetes check mode, the input device further configured to allow the user to select a fasting check mode or a postprandial check mode, wherein, based on the user's selections, the input device is configured to change an operational mode of said device to one of: a fasting diabetes check mode in which said at least one processor compares a blood glucose concentration with a range of predetermined values of fasting blood glucose levels indicative of diabetes stored in said at least one memory device, a postprandial diabetes check mode in which said at least one processor compares a blood glucose concentration with a range of predetermined values of postprandial blood glucose levels indicative of diabetes stored in said at least one memory device, a fasting prediabetes check mode in which said at least one processor compares the blood glucose concentration with a range of predetermined values of fasting blood glucose levels indicative of prediabetes stored in said at least one memory device, and a postprandial prediabetes check mode in which said at least one processor compares the blood glucose concentration with a range of predetermined values of postprandial blood glucose levels indicative of prediabetes stored in said at least one memory device, and an output device connected to said at least one processor and configured to show messages generated by said at least one processor, wherein said device prompts the user to select either diabetic or nondiabetic and then to select either fasting or postprandial, wherein in response to said user selecting non diabetic and fasting, the device is configured to operate in the fasting prediabetes check mode, and said at least one program stored in said at least one memory device causes the at least one processor to perform the following steps: cause said condition sensor to sense the blood glucose level of the user, calculate the blood glucose concentration based on the sensed blood glucose level, compare the blood glucose concentration with the range of predetermined values of fasting blood glucose levels indicative of prediabetes stored in said at least one memory device, determine if said user has prediabetes based on said comparison, and cause the output device to alarm or advise said user to check with a physician if prediabetes is detected.

2. The device of claim 1, wherein the output device alarms or advises said user to check with a physician if prediabetes is detected by text messages and visual alarms.

* * * * *